(12) United States Patent
Shiomi et al.

(10) Patent No.: US 6,603,029 B1
(45) Date of Patent: Aug. 5, 2003

(54) PARTIALLY PROTECTED NOVEL TRISPHENOLS AND PROCESS FOR PRODUCTION THEREOF

(75) Inventors: Taiichi Shiomi, Wakayama (JP); Sachiko Miyagi, Wakayama (JP); Toru Masuda, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 09/673,886

(22) PCT Filed: Feb. 24, 2000

(86) PCT No.: PCT/JP00/01079

§ 371 (c)(1),
(2), (4) Date: Dec. 18, 2000

(30) Foreign Application Priority Data

Feb. 25, 1999 (JP) .............................. 11-049016
Sep. 1, 1999 (JP) .............................. 11-247755

(51) Int. Cl.⁷ .......................... C09B 11/04; C09B 11/06
(52) U.S. Cl. ...................................... 552/101; 552/115
(58) Field of Search ................................ 552/101, 115

(56) References Cited

FOREIGN PATENT DOCUMENTS

| EP | 100158 | 2/1984 |
|----|--------|--------|
| EP | 733631 | 9/1996 |
| JP | 11-35509 | 2/1999 |
| WO | WO 95/05376 | 2/1995 |
| WO | WO 96/18626 | 6/1996 |
| WO | WO 98/57922 | 12/1998 |

*Primary Examiner*—Paul J. Killos
(74) *Attorney, Agent, or Firm*—Merchant & Gould P.C.

(57) ABSTRACT

The invention provides a partially protected trisphenol having the general formula (I)

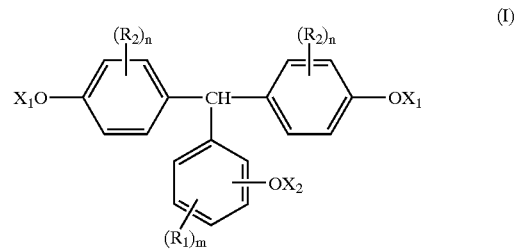

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_1$ is a hydrogen atom, an alkoxycarbonylmethyl group wherein the alkyl group has 1–4 carbons, an alkoxycarbonyl group wherein the alkyl group has 1–4 carbons or a tetrahydropyranyl group, $X_2$ is a hydrogen atom, an alkoxycarbonylmethyl group wherein the alkyl group has 1–4 carbons, an alkoxycarbonyl group wherein the alkyl group has 1–4 carbons or a tetrahydropyranyl group, provided that when $X_1$ is a hydrogen atom, $X_2$ is not a hydrogen atom, and when $X_2$ is a hydrogen atom, $X_1$ is not a hydrogen atom; and m is an integer of 0, 1 or 2, and n is an integer of 0, 1, 2 or 3.

7 Claims, 2 Drawing Sheets

PARTIALLY PROTECTED NOVEL TRISPHENOLS AND PROCESS FOR PRODUCTION THEREOF

FIELD OF THE INVENTION

This invention relates to partially protected novel trisphenols and a process for production thereof. More particularly, the invention relates to partially protected trisphenols in which only specifically selected one or two of the three hydroxyl groups are protected with a protecting agent and which are suitable for use as a dissolution inhibitor in chemically amplified photoresists and a process for the production of such specifically partially protected trisphenols.

The invention further relates to novel alkoxycarbonyl-methoxybenzaldehydes useful as raw materials for the production of monoalkoxycarbonylmethyl ethers of trisphenols, as one of the above-mentioned partially protected trisphenols, wherein one of the hydroxyl groups of the trisphenols is protected with an alkoxycarbonylmethyl group.

DESCRIPTION OF THE RELATED ART

It is widely known to micro-fabricate semiconductors by using positive photoresists. In recent years, integrated circuits are more and more integrated and such ultrafine pattern fabrication is needed wherein lines have a width of a half micron or less for the production of VLSI (very large scale integrated) semiconductor circuits. To acchieve such a high resolution, the wavelength of radiation for use in photolithography is more and more shortened, and at present, investigation for practical use of even far ultraviolet rays or excimer laser rays (such as XeCl, KrF or ArF) are carried out.

However, when a conventional positive photoresist comprising a novolak resin and a naphthoquinone diazide compound is used for pattern formation in the photolithography using far ultraviolet rays or excimer laser rays, the rays can hardly reach the bottom of the photoresist layer due to the strong absorption of the novolak resin and naphthoquinone diazide in the far ultraviolet and excimer laser radiation region. As results, fine and accurate patters cannot be formed.

To overcome this problem, a chemically amplified resist composition is proposed. Two component positive photoresist and three component positive photoresist are known as the chemically amplified resist composition. For example, the three component positive photoresist comprises a photoresist composed of a compound which generates an acid (acid generator) upon exposure to radiation and an alkali-isoluble polymer (base polymer) such as poly(p-hydroxystyrene) combined with a so-called acid-decomposable dissolution inhibitor. When a layer of the three component positive photoresist is exposed to far ultraviolet rays or excimer laser rays, the acid generator generates an acid in the exposed area and then the reaction of the dissolution inhibitor is caused by making use of the acid as a catalyst. Thus, the solubility of the photoresist is increased in an alkaline developer only in the exposed area so that a positive pattern with high contrast is formed.

As the basic requisites, the acid-decomposable dissolution inhibitor should be permeable (or transparent) to radiation such as far ultraviolet rays or excimer laser rays and compatible with solvents of photoresists or base polymers, and in addition, it should have resistance to etching at pattern portions when being developed. However, no such dissolution inhibitor as to fulfil all the requisites has been known heretofore.

After intensive investigations to solve the problems involved in the known chemically amplified photoresist compositions, the present inventors have found that partially protected trisphenols in which only one or two of the three hydroxyl groups of the trisphenols are protected fulfil all the above-mentioned requisites, and thus completed the invention.

Accordingly, it is an object of the invention to provide a partially protected trisphenol suitable for use as an acid-decomposable dissolution inhibitor in the chemically amplified photoresist compositions.

Furthermore, the etherification of hydroxyl group of trisphenol is hitherto effected by a condensation reaction of the trisphenol with a haloacetic acid ester. However, according to this method, it is not possible to etherify selectively a specific one of the three hydroxyl groups of the trisphenol. For example, if one third molar part of etherification agent is used per molar part of trisphenol, it is not possible to etherify selectively only a specific one of the three hydroxyl groups of the trisphenol.

The inventors have further found that the hydroxyl group of a hydroxybenzaldehyde is first benzyl-etherificated and is then condensed with a phenol, thereby providing a trisphenol in which a specifically selected hydroxyl group only is benzyl-etherificated, and that after protecting the remaining two hydroxyl groups with a protecting agent, the benzyl ether is subjected to hydrogenolysis, thereby readily providing a trisphenol in which only specifically selected two of the hydroxyl groups of the trisphenol are protected with a protecting agent.

Therefore, the invention provides, as a first aspect, a process for the production of partially protected trisphenols wherein specifically selected two hydroxyl groups only are protected with a protecting agent.

The inventors have still further found that a hydroxybenzaldehyde is first protected at its hydroxyl group, for example, as an alkoxycarbonylmethyl ether, and is then condensed with a phenol, thereby readily providing a monoalkoxycarbonylmethyl ether of trisphenol in which only one specifically selected hydroxyl group of the trisphenol is etherificated.

Therefore, the invention provides, as a second aspect, a process for the production of the above-mentioned monoalkoxycarbonylmethyl ether of trisphenol.

Furthermore, the invention provides, as a third aspect, an alkoxycarbonylmethoxybenzaldehyde, a novel compound, useful as a raw material for the production of the above-mentioned monoalkoxycarbonylmethyl ether of trisphenol.

SUMMARY OF THE INVENTION

The invention provides a partially protected trisphenol having the general formula (I)

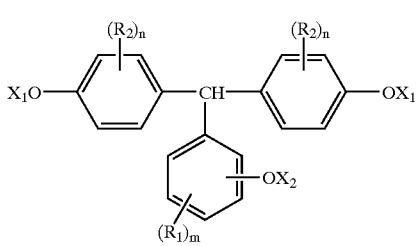

(I)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_1$ is a hydrogen atom, an alkoxycarbonylmethyl group wherein the alkyl group has 1–4 carbons, an alkoxycarbonyl group wherein the alkyl group has 1–4 carbons or a tetrahydropyranyl group, $X_2$ is a hydrogen atom, an alkoxycarbonylmethyl group wherein the alkyl group has 1–4 carbons, an alkoxycarbonyl group wherein the alkyl group has 1–4 carbons or a tetrahydropyranyl group, provided that when $X_1$ is a hydrogen atom, $X_2$ is not a hydrogen atom, and when $X_2$ is a hydrogen atom, $X_1$ is not a hydrogen atom; and m is an integer of 0, 1 or 2, and n is an integer of 0, 1, 2 or 3.

Namely, the invention provides a first partially protected trisphenol having the general formula (Ia)

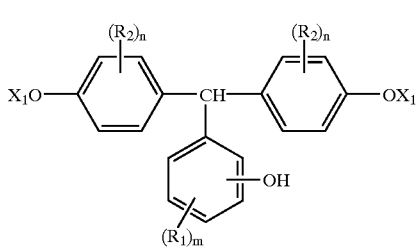

(Ia)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_1$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and n is an integer of 0, 1, 2 or 3.

According to the invention, the first partially protected trisphenol having the general formula (Ia) is obtained by a process which comprises:

the first step wherein a hydroxybenzaldehyde having the general formula (II)

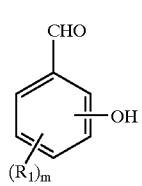

(II)

wherein $R_1$ is an alkyl group of 1–4 carbons or an alkoxyl group of 1–4 carbons; and m is an integer of 0, 1 or 2, and when m is 2, $R_1$'s may be the same or different from each other, is reacted with a benzyl halide in the presence of an alkali, to prepare a benzyloxybenzaldehyde having the general formula (III)

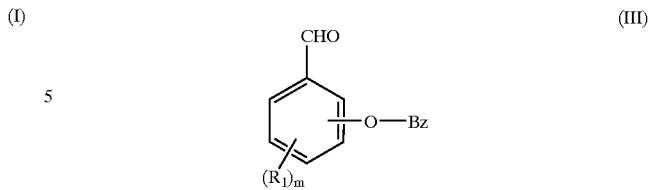

(III)

wherein $R_1$ and m are the same as hereinbefore defined, and Bz is a benzyl group;

the second step wherein the benzyloxybenzaldehyde is reacted with a phenol having the general formula (IV)

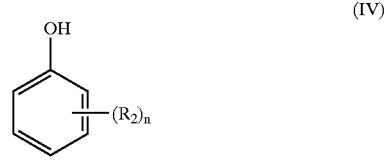

(IV)

wherein $R_2$ is an alkyl group of 1–6 carbons or a cycloalkyl group of 5 or 6 carbons; and n is an integer of 0, 1, 2 or 3, and when n is 2 or 3, $R_2$'s may be the same or different from each other, in the presence of an acid catalyst, to prepare a monobenzylated trisphenol having the general formula (V)

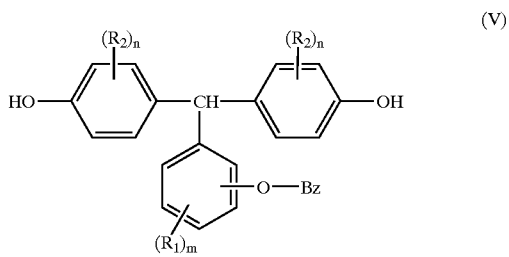

(V)

wherein $R_1$, $R_2$, Bz, m and n are the same as hereinbefore defined;

the third step wherein the monobenzylated trisphenol is reacted with a protecting agent selected from the group consisting of a haloacetic acid alkyl ester wherein the alkyl group has 1–4 carbons, a dialkyl carbonate wherein the alkyl group has 1–4 carbons and 2,3-dihydro-4-H-pyran, thereby protecting two hydroxyl groups in the molecule of the monobenzylated trisphenol, to prepare a trisphenol of which two hydroxyl groups are thus protected and which has the general formula (VI)

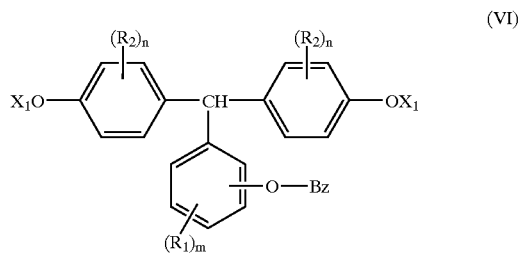

(VI)

wherein $R_1$, $R_2$, Bz, m and n are the same as hereinbefore defined; and $X_1$ is a protecting group selected from the group consisting of an alkoxycarbonylmethyl group wherein the alkyl group has 1–4 carbons, an alkoxycarbonyl group wherein the alkyl group has 1–4 carbons and a tetrahydropyranyl group; and the fourth step wherein the trisphenol of which two hydroxyl groups are protected is subjected to hydrogenolysis in the presence of a hydrogenolysis catalyst.

The invention further provides a second partially protected trisphenol having the general formula (Ib)

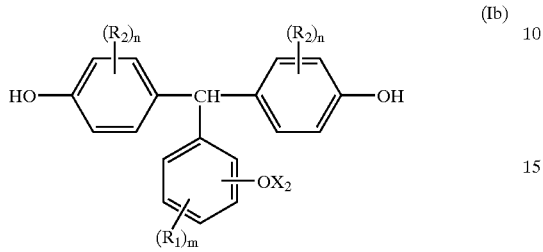

(Ib)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_2$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and n is an integer of 0, 1, 2 or 3.

Namely, the invention provides, as the second partially protected trisphenols, (i) a monoalkoxycarbonylmethoxytrisphenol having the general formula (Ic)

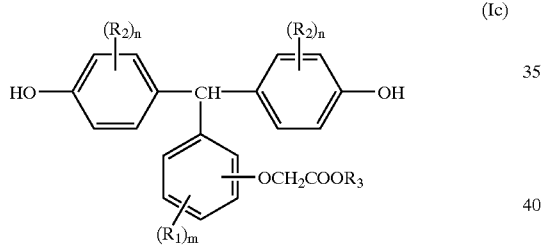

(Ic)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $R_3$ is an alkyl group of 1–4 carbons; and m is an integer of 0, 1 or 2, and n is an integer of 0, 1, 2 or 3; or (ii) a monoalkoxycarbonyloxytrisphenol having the general formula (Id)

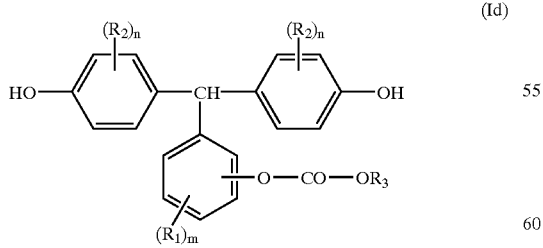

(Id)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $R_3$ is an alkyl group of 1–4 carbons; and m is an integer of 0, 1 or 2, and n is an integer of 0, 1, 2 or 3; or (iii) a monotetrahydropyranyloxytrisphenol having the general formula (Ie)

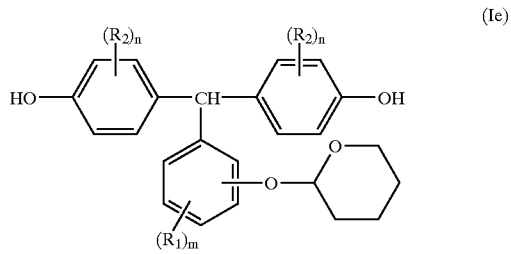

(Ie)

wherein $R_1$ is an alkyl group of 1–4 carbons or an alkoxyl group of 1–4 carbons, $R_2$ is an alkyl group of 1–6 carbons or a cycloalkyl group of 5 or 6 carbons; and m is an integer of 0, 1 or 2, and n is an integer of 0, 1, 2 or 3.

According to the invention, the second one of the partially protected trisphenols of the invention is obtained by reacting a benzaldehyde of which hydroxyl group is protected and which has the general formula (VII)

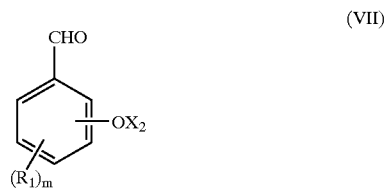

(VII)

wherein $R_1$ is an alkyl group of 1–4 carbons or an alkoxyl group of 1–4 carbons, $X_2$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and when m is 2, $R_1$'s may be the same or different from each other, with a phenol having the general formula (VIII)

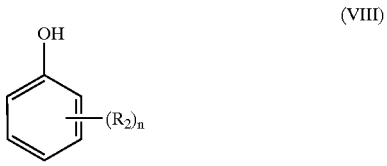

(VIII)

wherein $R_2$ is an alkyl group of 1–6 carbons or a cycloalkyl group of 5 or 6 carbons, $R_3$ is an alkyl group of 1–4 carbons; and n is an integer of 0, 1, 2 or 3, and when n is 2 or 3, $R_2$'s may be the same or different from each other, in the presence of an acid catalyst.

In addition, the invention provides an alkoxycarbonylmethoxybenzaldehyde having the general formula (IX)

(IX)

wherein $R_1$ is an alkyl group of 1–4 carbons or an alkoxyl group of 1–4 carbons, $R_3$ is an alkyl group of 1–4 carbons; and m is an integer of 0, 1 or 2, and when m is 2, $R_1$'s may be the same or different from each other.

DESCRIPTION OF PREFRRRED EMBODIMENTS OF THE INVENTION

Figure 1:
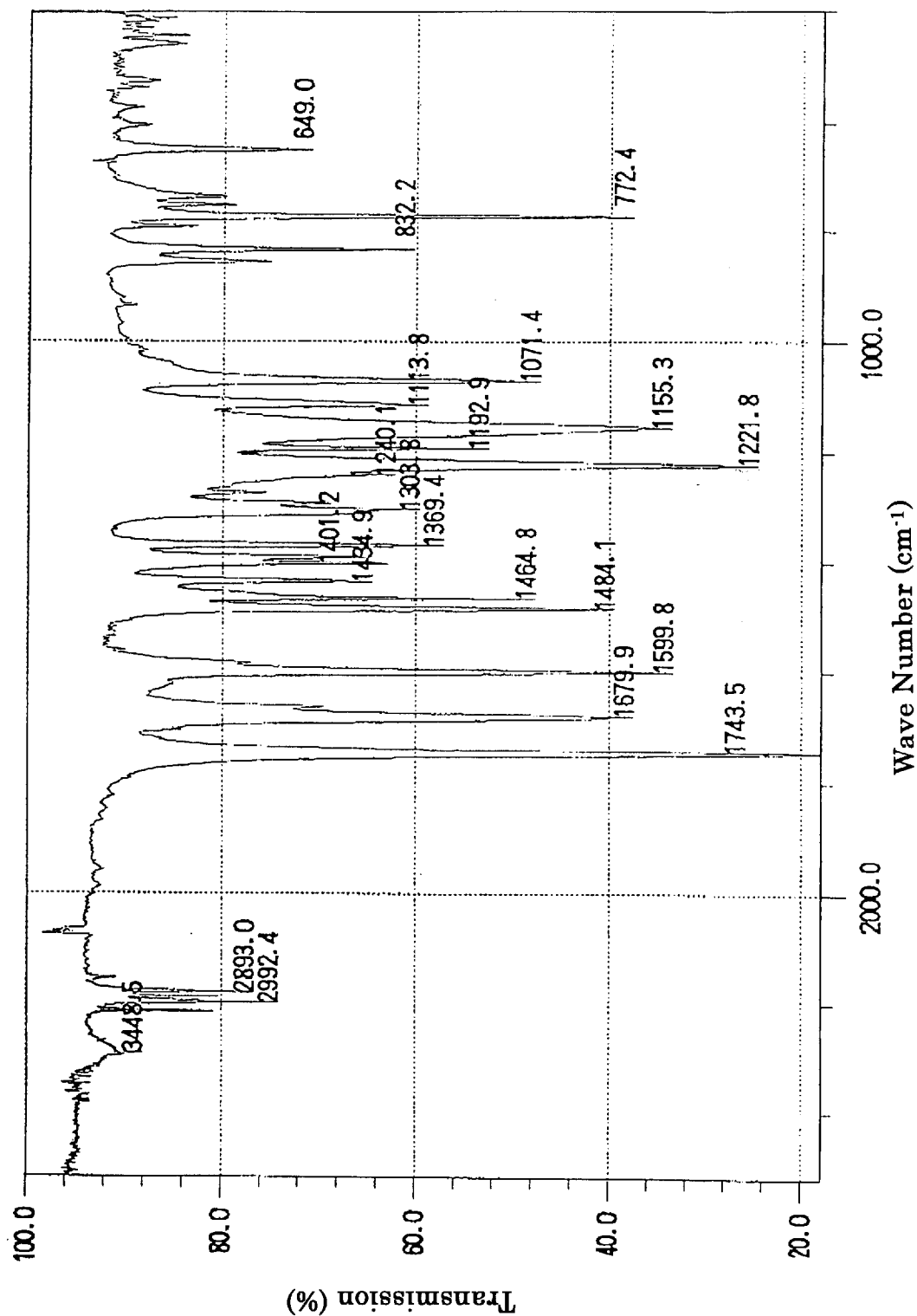
FIG. 1 is an infrared absorption spectrum of 2-t-butoxycarbonylmethoxybenzaldehyde of the invention.

The first one of the partially protected trisphenols of the invention is described. The first one of the partially protected trisphenols of the invention is represented by the general formula (Ia)

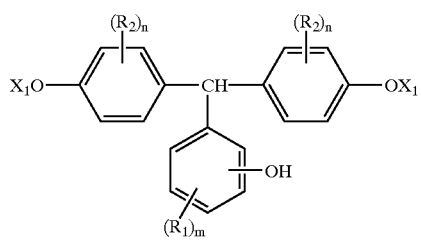
(Ia)

wherein $R_1$ is an alkyl group of 1–4 carbons or an alkoxyl group of 1–4 carbons, $R_2$ is an alkyl group of 1–6 carbons. or a cycloalkyl group of 5 or 6 carbons, $X_1$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and n is an integer of 0, 1, 2 or 3.

In the first one of the partially protected trisphenols of the invention having the general formula (Ia), $R_1$ is an alkyl group of 1–4 carbons or an alkoxyl group of 1–4 carbons. Accordingly, $R_1$ is, for example, such an alkyl group as a methyl, ethyl, propyl or butyl group or such an alkoxyl group as a methoxyl, ethoxyl, propoxyl or butoxyl group. When the alkyl group has three carbon atoms or more, it may be linear or branched. Similarly, when the alkoxyl group has three carbon atoms or more, the alkyl group contained in the alkoxyl group may also be linear or branched.

$R_2$ is an alkyl group of 1–6 carbons or a cycloalkyl group of 5 or 6 carbons. Accordingly, $R_2$ is, for example, such an alkyl group as a methyl, ethyl, propyl, butyl, pentyl or hexyl group or such a cycloalkyl group as a cyclopentyl or cyclohexyl group. When the alkyl group has three carbon atoms or more, it may be linear or branched. Furthermore, when m is 2, $R_1$'s may be the same or different from each other, and when n is 2 or 3, $R_2$'s may be the same or different from each other. However, it is in particular preferred that m is 0 or 1, and n is 1 or 2. When n is 2, it is preferred that one of two $R_2$'s is, for example, a methyl group, and the other is a cyclohexyl group.

In addition, in the above general formula (Ia), X is an alkoxycarbonylmethyl group wherein the alkyl group has 1–4 carbons, an alkoxycarbonyl group wherein the alkyl group has 1–4 carbons or a tetrahydropyranyl group, and preferably, X is a t-butoxycarbonylmethyl, t-butoxycarbonyl or a tetrahydropyranyl group.

Accordingly, some examples of the first one of the partially protected trisphenols of the invention are:

(1) 4,4'-bis(1-t-butoxycarbonylmethoxy-2-cyclohexyl-5-methylphenyl)methyl-2-hydroxybenzene,
(2) 4,4'-bis(1-t-butoxycarbonyloxy-2-cyclohexyl-5-methylphenyl)methyl-2-hydroxybenzene,
(3) 4,4'-bis(1-tetrahydropyranyloxy-2-cyclohexyl-5-methylphenyl)methyl-2-hydroxybenzene,
(4) 4,4'-bis(1-t-butoxycarbonylmethoxyphenyl)methyl-3-methoxy-4-hydroxybenzene.

The first one of the partially protected trisphenols of the invention is obtained by a process which comprises:

the first step wherein a hydroxybenzaldehyde having the general formula (II)

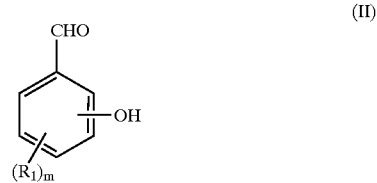
(II)

wherein $R_1$ is an alkyl group of 1–4 carbons or an alkoxyl group of 1–4 carbons; and m is an integer of 0, 1 or 2, and when m is 2, $R_1$'s may be the same or different from each other, is reacted with a benzyl halide in the presence of an alkali, to prepare a benzyloxybenzaldehyde having the general formula (III)

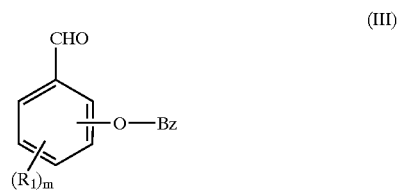
(III)

wherein $R_1$ and m are the same as hereinbefore defined, and Bz is a benzyl group;

the second step wherein the benzyloxybenzaldehyde is reacted with a phenol having the general formula (IV)

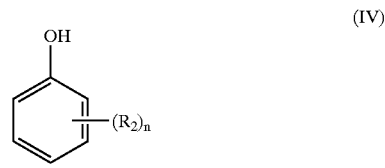
(IV)

wherein $R_2$ is an alkyl group of 1–6 carbons or a cycloalkyl group of 5 or 6 carbons; and n is an integer of 0, 1, 2 or 3, and when n is 2 or 3, $R_2$'s may be the same or different from each other, in the presence of an acid catalyst, to prepare a monobenzylated trisphenol having the general formula (V)

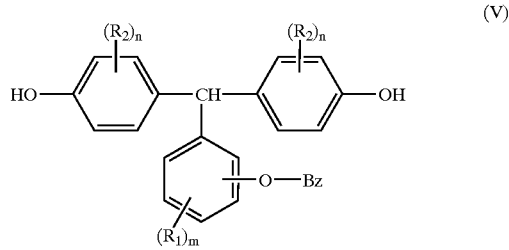
(V)

wherein $R_1$, $R_2$, Bz, m and n are the same as hereinbefore defined;

the third step wherein the monobenzylated trisphenol is reacted with a protecting agent selected from the group consisting of a haloacetic acid alkyl ester wherein the alkyl group has 1–4 carbons, a dialkyl carbonate wherein the alkyl group has 1–4 carbons and 2,3-dihydro-4-H-pyran, thereby protecting two hydroxyl groups in the molecule of the monobenzylated trisphenol, to prepare a trisphenol of which two hydroxyl groups are thus protected and which has the general formula (VI)

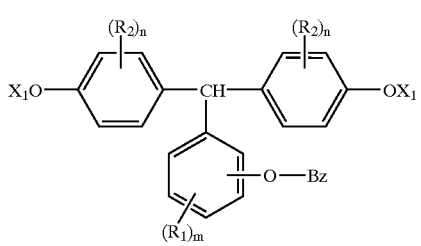

(VI)

wherein $R_1$, $R_2$, Bz, m and n are the same as hereinbefore defined; and $X_1$ is a protecting group selected from the group consisting of an alkoxycarbonylmethyl group wherein the alkyl group has 1–4 carbons, an alkoxycarbonyl group wherein the alkyl group has 1–4 carbons and a tetrahydropyranyl group; and the fourth step wherein the trisphenol of which two hydroxyl groups are protected is subjected to hydrogenolysis in the presence of a hydrogenolysis catalyst.

The steps for the production of the first one of the partially protected trisphenols of the invention is shown in the scheme below.

Scheme of Production of Partially Protected Trisphenol Having the General Formula (Ia)

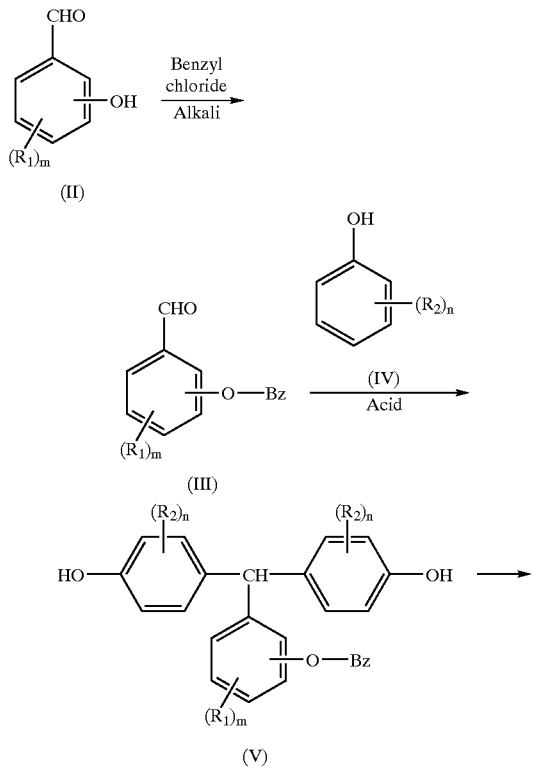

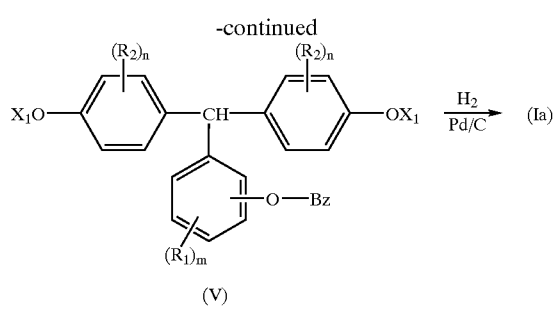

(Ia)

(V)

The first step for benzylation of hydroxybenzaldehydes having the general formula (II) is described.

In the hydroxybenzaldehydes having the general formula (II), $R_1$ is mentioned hereinbefore, and accordingly, preferred examples thereof include o-hydroxy-benzaldehyde, m-hydroxybenzaldehyde, p-hydroxybenzaldehyde or 3-methoxy-4-hydroxybenzaldehyde.

Monobenzylated trisphenols having the general formula (III) are obtained usually by reacting one molar part of the hydroxybenzaldehyde with one to two molar parts of a benzyl halide such as benzyl chloride in the presence of one to two molar parts of an alkali such as potassium carbonate in an organic solvent such as dimethylformamide. The reaction temperature is not specifically limited, but it is usuallyin the range of 30–120° C. and preferably in the range of 40–80° C.

After the reaction, an organic solvent such as toluene or methyl isobutyl ketone and water are added to the resulting reaction mixture to wash the mixture, a water layer is separated to leave an oily layer, and the oily layer is distilled to remove the organic solvent therefrom, thereby providing the reaction product as the distillation residual. Alternatively, the oily layer is concentrated by removing the organic solvent by distillation therefrom, and a hydrocarbon crystallization solvent such as n-heptane, n-hexane or toluene is added to the distillation residual, to effect crystallization, thereby providing the reaction product.

The second step is to prepare monobenzylated trisphenols by reacting the thus obtained benzyloxybenzaldehydes having the general formula (III) with the phenol having the general formula (IV).

In the phenol having the general formula (IV), $R_2$ and n are the same as those mentioned hereinabove, and as a particularly preferred example of such phenols, there is mentioned, for example, 2-cyclohexyl-5-methylphenol.

In the second step, the reaction of the benzyloxybenzaldehyde with the phenol is carried out usually in an alcoholic solvent in the presence of an acid catalyst by using 2–10 molar parts, preferably 2–6 molar parts of the phenol per molar part of the benzyloxybenzaldehyde.

As the above alcoholic solvent, lower aliphatic alcohols such as methanol, ethanol, isopropyl alcohol, n-propyl alcohol, t-butyl alcohol, isobutyl alcohol or n-butyl alcohol are used, in consideration of raw materials used in the reaction, solubility of the resulting reaction product, reaction conditions under which the reaction is carried out or economy of reaction process. Among the above, methanol is in particular preferred.

The alcoholic solvent is used usually in an amount of 10–1000 parts by weight, preferably in an amount of 20–400 parts by weight, per 100 parts by weight of the benzyloxybenzaldehyde used, although the amount of the alcoholic solvent used is not specifically limited.

The acid catalyst used is preferably such that it is suluble in the alcoholic solvent or the reaction solvent used. Therefore, for example, hydrochloric acid, sulfuric acid, sulfuric acid anhydride, p-toluenesulfonic acid, methanesulfonic acid, trifluoromethane sulfonic acid, oxalic acid, formic acid, phosphoric acid, trichloroacetic acid or trifluoroacetic acid are given as preferred examples. The acid catalyst, for example, 35% hydrochloric acid, is used in an amount of 1–500 parts by weight, preferably in an amount of 5–50 parts by weight, per 100 parts by weight of the benzyloxybenzaldehyde used.

The reaction is carried out in a nitrogen gas stream with stirring usually at a temperature of 0–90° C., preferably at a temperature of 0–50° C. for 1–72 hours, preferably for 1–24 hours.

After completion of the reaction, an alkali such as aqueous ammonia or an aqueous solution of sodium hydroxide is added to the resulting reaction mixture to neutralize the acid catalyst used, the resulting aqueous layer is separated, and the resulting oily layer is subjected to distillation under reduced pressure to remove the solvent therefrom. Water or an organic solvent such as, for example, aromatic hydrocarbons, aliphatic hydrocarbons or aliphatic ketones, or a mixture of these is added to the distillation residue as a crystallization solvent to dissolve the residue therein, followed by cooling the thus formed solution, thereby crystallizing the desired monobenzylated trisphenol of high purity.

Water is a good crystallization solvent for some of the monobenzylated trisphenols, while organic solvents are good crystallization solvents for others of the monobenzylated trisphenols. Among the organic solvents, aromatic hydrocarbons such as toluene, xylene or cumene, or aliphatic hydrocarbons such as n-pentane, n-hexane, isohexane, n-heptane, n-octane, isooctane, n-decane, 2,2-dimethylbutane, petroleum ether, petroleum benzin, ligroin, kerosene, petroleum spirit, petroleum naphtha, 2-pentene, mixed pentene, cyclohexane or methylcyclohexane, or aliphatic ketones such as isopropyl ketone, methyl ethyl ketone, methyl isobutyl ketone or diisopropyl ketone are used as crystallization solvents in consideration of crystallization conditions as well as effectiveness or economy of crystallization.

By the use of such crystallization solvents in an amount of 20–1000 parts by weight, preferably in an amount of 50–500 parts by weight, per 100 parts by weight of the reaction mixture, the desired monobenzylated trisphenols of high purity are crystallized out of the mixture. If necessary, the thus obtained monobenzylated trisphenols are recrystallized from the above-mentioned crystallization solvent to provide the desired monobenzylated trisphenols of higher purity.

The third step is to protect two hydroxyl groups of the thus obtained monobenzylated trisphenols with a protecting agent. As this protecting agent, a haloacetic acid alkyl ester wherein the alkyl group has 1–4 carbon atoms, a dialkyl carbonate wherein each of the alkyl groups has 1–4 carbon atoms or 2,3-dihydro-4-H-pyran is used.

The halogen atom in the haloacetic acid alkyl ester is preferably chlorine or bromine atoms, while the alkyl group is a methyl, ethyl, propyl or butyl group. When the alkyl group has three carbon atoms or more, it may be either linear or branched, however, it is particularly preferred that the alkyl group is a t-butyl group. Accordingly, preferred haloacetic acid alkyl esters includes, for example, t-butyl chloroacetate or t-butyl bromoacetate.

In the same manner, each of the alkyl groups in the dialkyl carbonates is a methyl, ethyl, propyl or butyl group, and when the alkyl group has three carbon atoms or more, it may be either linear or branched, however, it is particularly preferred that the alkyl group is a t-butyl group. Accordingly, di-t-butyl carbonate is one of preferred dialkyl carbonates.

In order to protect the two remaining hydroxyl groups of the monobenzylated trisphenols with a haloacetic acid alkyl ester or a dialkyl carbonate, one molar part of monobenzylated trisphenol is reacted with two to five molar parts of the haloacetic acid alkyl ester or dialkyl carbonate in the presence of an alkali such as potassium carbonate in an amount of 0.1–5 molar parts per molar part of monobenzylated trisphenol. The reaction is carried out usually at a temperature of 50–120° C. for several hours, for example, 2–20 hours.

After the reaction, the resulting reaction mixture is washed with an organic solvent, e.g., toluene or cyclohexane, and water, the resulting aqueous layer is separated, and the obtained organic layer, if necessary, after being washed with an aqueous acid solution and neutralized, is subjected to distillation to remove the solvent therefrom. An aliphatic lower alcohol such as methanol is then added to the resultant distillation residue and, if necessary, together with the hereinbefore mentioned aromatic hydrocarbons or aliphatic ketones, to crystallize the desired trisphenol of which two hydroxyl groups are protected with the above-mentioned protecting agent. Alternatively, the resulting reaction mixture is washed with an organic solvent and water, and then the washing solvents were removed by distillation, thereby providing the desired trisphenol of which two hydroxyl groups are protected with the protecting agent.

On the other hand, for the purpose of converting the two residual hydroxyl group of the monobenzylated trisphenols with 2,3-dihydro-4-H-pyran to tetrahydropyranyl ether, the monobenzylated trisphenols are reacted with 2,3-dihydro-4-H-pyran in the presence of an acid catalyst in an organic solvent such as ethyl acetate, tetrahydrofuran or methyl ethyl ketone.

2,3-Dihydro-4-H-pyran is used usually in an amount of 3–10 molar parts per molar part of the trisphenol. As the acid catalyst, p-toluenesulfonic acid, pyridinium p-toluenesulfonate, concentrated hydrochloric acid or concentrated sulfuric acid is used, for example. The reaction is carried out usually at a temperature of 0–25° C. for from several minutes to dozens of hours.

When the reaction is completed in this way, the desired trisphenol in which two hydroxyl group are converted to tetrahydropyranyl ether is obtained as crystals in some cases, However, in other cases, after the completion of the reaction, the reaction mixture is washed and neutralized with an aqueous alkaline solution, and the aqueous layer is removed therefrom, and the organic layer is subjected to distillation under reduced pressure to remove the solvent. Then the resulting distillation residue is purified by using columns thereby providing the desired product.

Finally, in the fourth step, the thus obtained desired trisphenol in which two hydroxyl group are protected is dissolved in an organic solvent, e.g., tetrahydrofuran, and is subjected to hydrogenolysis by blowing hydrogen into the solution at atmospheric pressure in the presence of a hydrogenolysis catalyst, thereby providing the desired trisphenols in which the desired two only of the three hydroxyl groups are protected while the third hydroxyl group remains free. The hydrogenolysis catalyst used is preferably palladium/ carbon powder, for example. The reaction temperature is not specifically limited, but it is usually in the range of 0–80° C.

After the reaction, by way of example, the resulting reaction mixture is filtered to remove the catalyst used therefrom, and is then subjected to distillation under reduced pressure to remove the solvent, to provide the desired product as a distillation residue. Alternatively, after the removal of the solvent, a crystallization solvent is added to the distillation residue to crystallize the desired product from the solvent.

The second one of the partially protected trisphenols of the invention is in turn described. The second one of the partially protected trisphenols of the invention has the general formula (Ib)

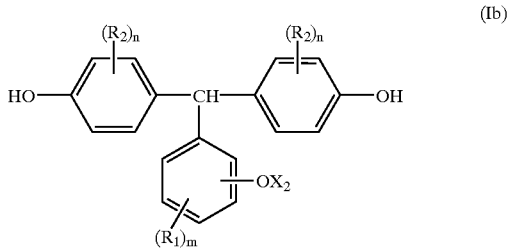

(Ib)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_2$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and n is an integer of 0, 1, 2 or 3.

That is, the invention provides, as the second partially protected trisphenol, (i) a monoalkoxycarbonylmethoxytrisphenol having the general formula (Ic)

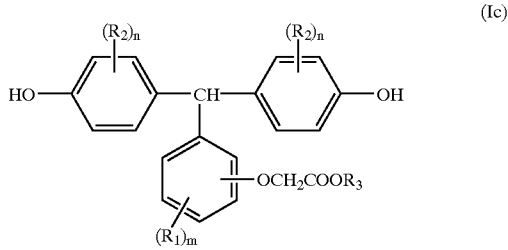

(Ic)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $R_3$ is an alkyl group of 1–4 carbons; and m is an integer of 0, 1 or 2, and n is an integer of 0, 1, 2 or 3; or (ii) a monoalkoxycarbonylmethoxytrisphenol having the general formula (Id)

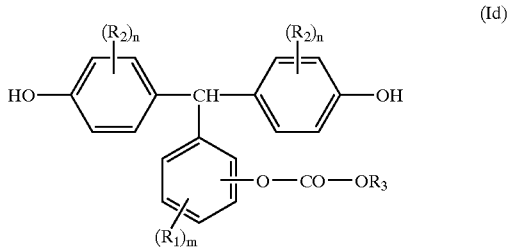

(Id)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $R_3$ is an alkyl group of 1–4 carbons; and m is an integer of 0, 1 or 2, and n is an integer of 0, 1, 2 or 3; or (iii) a monotetrahydropyranyloxytrisphenol having the general formula (Ie)

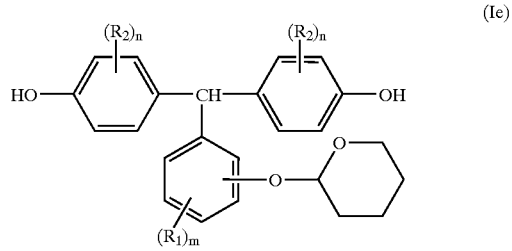

(Ie)

wherein $R_1$ is an alkyl group of 1–4 carbons or an alkoxyl group of 1–4 carbons, $R_2$ is an alkyl group of 1–6 carbons or a cycloalkyl group of 5 or 6 carbons: and m is an integer of 0, 1 or 2, and n is an integer of 0, 1, 2 or 3.

In the second partially protected trisphenols having the general formula (Ic), (Id) or (Ie), $R_1$ is an alkyl group of 1–4 carbons or an alkoxyl group of 1–4 carbons. Accordingly, $R_1$ is, for example, such an alkyl group as a methyl, ethyl, propyl or butyl group or such an alkoxyl group as a methoxyl, ethoxyl, propoxyl or butoxyl group. When the alkyl group has three carbon atoms or more, it may be linear or branched. Similarly, when the alkoxyl group has three carbon atoms or more, the alkyl group contained in the alkoxyl group may also be linear or branched.

$R_2$ is an alkyl group of 1–6 carbons or a cycloalkyl group of 5 or 6 carbons. Accordingly, $R_2$ is, for example, such an alkyl group as a methyl, ethyl, propyl, butyl, pentyl or hexyl group or such a cycloalkyl group as a cyclopentyl or cyclohexyl group. When the alkyl group has three carbon atoms or more, it may be linear or branched. Furthermore, when m is 2, $R_1$'s may be the same or different from each other, and when n is 2 or 3, $R_2$'s may be the same or different from each other. However, it is in particular preferred that m is 0 or 1, and n is 1 or 2. When n is 2, it is preferred that one of two $R_2$'s is, for example, a methyl group, and the other is a cyclohexyl group.

$R_3$ is an alkyl group of 1–4 carbons, and exemplified by a methyl, ethyl, propyl or butyl group. When the alkyl group has three carbon atoms or more, it may be linear or branched. However, it is preferred that $R_3$ is a t-butyl group.

Accordingly, there may be mentioned 4,4'-bis(1-hydroxy-2-cyclohexyl-5-methylphenyl)methyl-2-t-butoxycarbonylmethoxybenzene as a preferred example of the monoalkoxycarbonylmethoxytrisphenols (Ic) of the invention.

There may be mentioned 4,4'-bis(1-hydroxy-2-cyclohexyl-5-methylphenyl)methyl-2-t-butoxycarbonyloxybenzene as a preferred example of the monoalkoxycarbonyloxytrisphenols (Id) of the invention, and there may be mentioned 4,4'-bis(1-hydroxy-2-cyclohexyl-5-methylphenyl)methyl-2-tetrahydropyranyloxybenzene as a preferred example of the monotetrahydropyranyloxytrisphenols (Ie) of the invention.

The second one of the partially protected trisphenols of the invention is obtained by reacting a benzaldehyde of which hydroxyl group is protected and which has the general formula (VII)

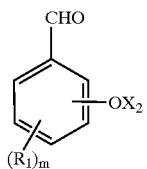

(VII)

wherein $R_1$ is an alkyl group of 1–4 carbons or an alkoxyl group of 1–4 carbons, $X_2$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and when m is 2, $R_1$'s may be the same or different from each other, with a phenol having the general formula (VIII)

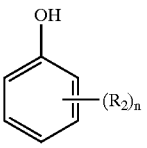

(VIII)

wherein $R_2$ is an alkyl group of 1–6 carbons or a cycloalkyl group of 5 or 6 carbons, $R_3$ is an alkyl group of 1–4 carbons; and n is an integer of 0, 1, 2 or 3, and when n is 2 or 3, $R_2$'s may be the same or different from each other, in the presence of an acid catalyst.

In more detail, the monoalkoxycarbonylmethoxytrisphenols are obtained according to the invention by reacting an alkoxycarbonylmethoxybenzaldehyde having the general formula (IX)

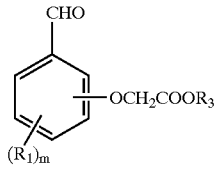

(IX)

wherein $R_1$ is an alkyl group of 1–4 carbons or an alkoxyl group of 1–4 carbons, $R_3$ is an alkyl group of 1–4 carbons; and m is an integer of 0, 1 or 2, and when m is 2, $R_1$'s may be the same or different from each other, with a phenol having the general formula (VIII)

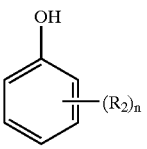

(VIII)

wherein $R_2$ is an alkyl group of 1–6 carbons or a cycloalkyl group of 5 or 6 carbons; and n is an integer of 0, 1, 2 or 3, and when n is 2 or 3, $R_2$'s may be the same or different from each other, in the presence of an acid catalyst.

In the alkoxycarbonylmethoxybenzaldehyde represented by the general formula (IX), $R_3$ is an alkyl group of 1–4 carbons, as hereinbefore mentioned, and accordingly, $R_3$ is, for example, a methyl, ethyl, propyl or butyl group. When the alkyl group has three carbon atoms or more, it may be linear or branched.

Similarly, $R_1$ is an alkyl group of 1–4 carbons or an alkoxyl group of 1–4 carbons. Accordingly, $R_1$ is, for example, such an alkyl group as a methyl, ethyl, propyl or butyl group or such an alkoxyl group as a methoxyl, ethoxyl, propoxyl or butoxyl group. When the alkyl group has three carbon atoms or more, it may be linear or branched, and when the alkoxyl group has three carbon atoms or more, the alkyl group contained in the alkoxyl group may also be linear or branched.

Accordingly, there may be mentioned 2-t-butoxycarbonylmethoxybenzaldehyde, 4-t-butoxycarbonylmethoxybenzaldehyde or 3-t-butoxycarbonylmethoxybenzaldehyde as preferred examples of the alkoxycarbonylmethoxybenzaldehydes of the invention.

The reaction of the alkoxycarbonylmethoxybenzaldehyde with the phenol having the general formula (VIII) is carried out usually in an alcoholic solvent in the presence of an acid catalyst by using two molar parts or more, preferably 2–10 molar parts, most preferably 3–6 molar parts, of the phenol, per molar part of the alkoxycarbonylmethoxybenzaldehyde.

As the above alcoholic solvent, lower aliphatic alcohols such as methanol, ethanol, isopropyl alcohol, n-propyl alcohol, t-butyl alcohol, isobutyl alcohol or n-butyl alcohol are used, in consideration of raw materials used in the reaction, solubility of the resulting reaction product, reaction conditions under which the reaction is carried out or economy of reaction process. Among the above, methanol is in particular preferred.

The alcoholic solvent is used usually in an amount of 10–1000 parts by weight, preferably in an amount of 40–400 parts by weight, per 100 parts by weight of the alkoxycarbonylmethoxybenzaldehyde used, although the amount of the alcoholic solvent used is not specifically limited.

The acid catalyst used is preferably soluble in the alcoholic solvent or the reaction solvent used. Therefore, for example, hydrochloric acid, sulfuric acid, sulfuric acid anhydride, p-toluenesulfonic acid, methanesulfonic acid, trifluoromethanesulfonic acid, oxalic acid, formic acid, phosphoric acid, trichloroacetic acid or trifluoroacetic acid are given as preferred examples. The acid catalyst, for example, 35% hydrochloric acid, is used in an amount of 1–500 parts by weight, preferably in an amount of 20–100 parts by weight, per 100 parts by weight of the alkoxycarbonylmethoxybenzaldehyde used.

The reaction is carried out in a nitrogen gas stream with stirring usually at a temperature of 0–80° C., preferably at a temperature of 0–50° C., for 1–72 hours, preferably for 1–24 hours.

After completion of the reaction, an alkali such as aqueous ammonia or an aqueous solution of sodium hydroxide is added to the resulting reaction mixture to neutralize the acid catalyst used, the resulting aqueous layer is separated, and the resulting oily layer is subjected to distillation under reduced pressure to remove the solvent therefrom. Then an aromatic hydrocarbon, aliphatic hydrocarbons or aliphatic ketones, or a mixture of these is added to the distillation residue as a crystallization solvent to dissolve the residue therein, followed by cooling the thus formed solution, thereby crystallizing the desired monoalkoxycarbonylmethoxytrisphenol of high purity out of the solvent.

Among the above-mentioned crystallization solvents, aromatic hydrocarbons such as toluene, xylene or cumene, or aliphatic hydrocarbons such as n-pentane, n-hexane, isohexane, n-heptane, n-octane, isooctane, n-decane, 2,2- dimethylbutane, petroleum ether, petroleum benzin, ligroin, kerosene, petroleum spirit, petroleum naphtha, 2-pentene, mixed pentene, cyclohexane or methylcyclohexane, or aliphatic ketones such as isopropyl ketone, methyl ethyl ketone, methyl isobutyl ketone or diisopropyl ketone are used as crystallization solvents in consideration of crystallization conditions as well as effectiveness or economy of crystallization.

By the use of such crystallization solvents in an amount of 20–1000 parts by weight, preferably in an amount of 50–500 parts by weight, per 100 parts by weight of the reaction mixture, the desired monoalkoxycarbonylmethylated trisphenol of high purity is crystallized out of the mixture. If necessary, the thus obtained product is recrystallized from the above-mentioned crystallization solvent to provide a product of higher purity The alkoxycarbonylmethoxybenzaldehydes used as raw materials for the production of the monoalkoxycarbonylmethoxytrisphenol of the invention are also novel organic compounds. The alkoxycarbonylmethoxybenzaldehyde is obtained by reacting the corresponding hydroxybenzaldehydes having the general formula (XII)

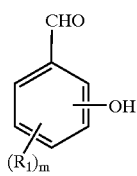

(XII)

wherein $R_1$ is an alkyl group of 1–4 carbons or an alkoxyl group of 1–4 carbons, and m is 0, 1 or 2, and when m is 2, $R_1$'s may be the same or different from each other, with a t-butyl haloacetate such as t-butyl chloroacetate or t-butyl bromoacetate in the presence of potassium carbonate in an organic solvent, e.g., dimethylformamide.

The t-butyl haloacetate is used usually in an amount of 1–5 molar parts per molar part of the hydroxybenzaldehyde, while potassium carbonate is used usually in an amount of 1–3 molar parts per molar part of the hydroxybenzaldehyde. The reaction is carried out usually at a temperature of 30–120° C. for a period of several hours, e.g., for 2–20 hours.

After the reaction, the resultant reaction mixture is washed with a mixture of an organic solvent, for example, such as toluene or cyclohexane and water, and the resulting aqueous layer is removed. Then, if necessary, after the resulting organic layer is washed and neutralized with an aqueous solution of an acid, the organic layer is distilled to remove the solvent therefrom. An aliphatic lower alcohol such as methanol or an aliphatic hydrocarbon such as n-heptane is added to the resulting distillation residue to effect crystallization or distill away the solvent from the resulting solution, thereby providing the desired alkoxycarbonylmethoxybenzaldehyde.

The partially protected trisphenols represented by the general formula (Id) or (Ie) are also obtained in the same manner as the partially protected trisphenols represented by the general formula (Ia).

More specifically, the monoalkoxycarbonyloxytrisphenols having the general formula (Id) are obtained according to the invention by reacting an alkoxycarbonyloxybenzaldehyde having the general formula (X)

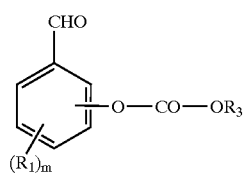

(X)

wherein $R_1$ is an alkyl group of 1–4 carbons or an alkoxyl group of 1–4 carbons, $R_3$ is an alkyl group of 1–4 carbons; and m is an integer of 0, 1 or 2, and when m is 2, $R_1$'s may be the same or different from each other, with the hereinbefore mentioned phenol having the general formula (VIII) in the presence of an acid catalyst.

The alkoxycarbonyloxybenzaldehyde is obtained by reacting the corresponding hydroxybenzaldehyde, that is, the hydroxybenzaldehyde represented by the general formula (XII), with a dialkyl carbonate such as di-t-butyl carbonate in the presence of a catalytic amount of potassium carbonate in a reaction solvent such as toluene. The dialkyl carbonate is used usually in an amount of 1–3 molar parts per molar part of the hydroxybenzaldehyde used. The reaction is carried out usually at a temperature of 30–120° C. for a period of several hours, e.g., for 2–20 hours.

After completion of the reaction, the reaction mixture is treated in the same manner as in the production of the alkoxycarbonylmethoxybenzaldehydes, thereby providing the desired alkoxycarbonyloxybenzaldehyde.

As a preferred example of the alkoxycarbonyloxybenzaldehydes, there may be mentioned 2-t-butoxycarbonyloxybenzaldehyde.

In the same manner, the monotetrahydropyranyloxytrisphenols having the general formula (Ie) are obtained according to the invention by reacting a tetrahydropyranyloxybenz aldehydehaving the general formula (XI)

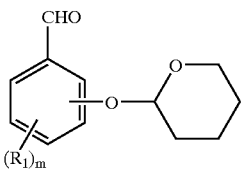

(XI)

wherein $R_1$ is an alkyl group of 1–4 carbons or an alkoxyl group of 1–4 carbons; and m is an integer of 0, 1 or 2, and when m is 2, $R_1$'s may be the same or different from each other, with the hereinbefore mentioned phenol having the general formula (VIII) in the presence of an acid catalyst.

The tetrahydropyranyloxybenzaldehyde is obtained by reacting the corresponding hydroxybenzaldehyde, that is, the hydroxybenzaldehyde represented by the general formula (XII), with 2,3-dihydro-4-H-pyran in the presence of an acid catalyst such as p-toluenesufonic acid in a reaction solvent such as tetrahydrofuran or ethyl acetate. The amount of 2,3-dihydro-4-H-pyran used is usually in the range of 1–3 molar parts per molar part of the hydroxybenzaldehyde used. The reaction is carried out usually at a temperature of 30–120° C. for a period of several hours, e.g., for 2–20 hours.

After completion of the reaction, the reaction mixture is treated in the same manner as in the production of the alkoxycarbonylmethoxybenzaldehydes, thereby providing the desired tetrahydropyranyloxybenzaldehyde.

As a preferred example of the tetrahydropyranyloxybenzaldehydes, there may be mentioned 2-tetrahydropyranyloxybenzaldehyde.

In general, it is easy to protect all of the hydroxyl groups of a trisphenol with a protecting agent, but it is very difficult to protect only a part of hydroxy groups of a trisphenols with a protecting agent. It is practically impossible to obtain in a high yield a high purity partially protected trisphenol in which only specifically selected one or two of the three hydroxyl groups of the trisphenol are protected with a protecting agent.

However, according to the invention, a hydroxybenzaldehyde is first benzylated at its hydroxyl group, that is, the hydroxybenzaldehyde is converted to a benzyl ether, and then the benzyl ether is condensed with a phenol to prepare a trisphenol in which only one specifically selected hydroxyl group is benzylated. Then, after the remained two hydroxyl groups of the trisphenol are protected with a protecting agent, the benzyl ether group of the trisphenol compound is subjected to hydrogenolysis. In this way, the first one of the partially protected trisphenol of the invention in which only specifically selected two of the three hydroxyl groups are protected is readily obtained according to the process of the invention.

In addition, the first one of the partially protected trisphenols of the invention, in particular, a partially protected trisphenol which is t-butoxycarbonylmethyl etherified or t-butoxycarbonylated or tetrahydropyranyl etherified at its two hydroxyl groups have a single hydroxyl group in the molecule. Accordingly, such a partially protected trisphenol is compatible with a solvent or a base polymer for photoresists so that it is useful as an acid-decomposable dissolution inhibitory agent, as hereinbefore described.

Further, the first one of the partially protected trisphenols of the invention are also suitable for use as a dissolution controlling agent for photoresists by using in combination with trisphenols in which all the hydroxyl groups are protected or trisphenols in which the hydroxyl groups are protected otherwise.

As a further aspect of the invention, the hydroxyl group of hydroxybenzaldehyde is first protected with an alkoxycarbonylmethyl group and the thus hydroxyl group protected hydroxybenzaldehyde is then condensed with a phenol, to provide the second one of the partially protected trisphenols of the invention easily. Preferred examples thereof are monoalkoxycarbonylmethyl ethers of trisphenols, in particular, t-butoxycarbonylmethyl ethers.

The monoalkoxycarbonylmethyl ethers of trisphenols of the invention, in particular, t-butoxycarbonylmethyl ethers, have two hydroxyl groups as well as a t-butoxycarbonylmethoxyl group in the molecule and they are compatible with a solvent or a base polymer for photoresists so that they are useful as acid-decomposable dissolution inhibitory agent. Besides, they are useful as a dissolution controlling agent for photoresists by using in combination with an acid-decomposable dissolution inhibitory agent or a trisphenol in which all the hydroxyl groups are protected in the form of alkoxycarbonylmethyl ether.

EXAMPLES

The invention will now be described with reference to examples, but the invention is not limited to these examples.

Production of the First one of the Partially Protected Trisphenols of the Invention Example 1

(Production of 4,4'-bis(1-t-Butoxycarbonylmethoxy-2-cyclohexyl-5-methylphenyl)-2-hydroxybenzene (1))

First Step (Production of 2-Benzyloxybenzaldehyde)

185 g of dimethylformamide and 82.8 g (0.6 mol) of potassium carbonate were placed in a flask, and 61 g (0.5 mol) of salicylaldehyde were added dropwise thereto. 75.9 g (0.6 mol) of benzyl chloride were then added dropwise to the resulting mixture at a temperature of 50° C. for one hour. After the addition, the mixture was stirred at a temperature of 70° C. for two hours. The resulting reaction mixture was washed with 185 g of toluene and 330 g of water. The solvent was distilled out of the mixture at an inside temperature of 90° C. under a reduced pressure of 10 mmHg thereby providing 104.5 g of 2-benzyloxybenzaldehyde as bottom in the form of brown liquid having a purity 97.9% in a yield of 96.5%.

Second Step (Production of 4,4'-bis(1-Hydroxy-2-cyclohexyl-5-methylphenyl) methyl-2-benzyloxybenzene)

201 g of 2-cyclohexyl-5-methylphenol (1.06 mol), 50 g of methanol and 10 g of 35% hydrochloric acid were placed in a flask. A solution of 97.3 g (0.46 mol) of 2-benzyloxybenzaldehyde in 24 g of methanol was added dropwise to the mixture for two hours at a temperature of 60° C. After the addition, the mixture was stirred for three hours at a temperature of 60° C., whereupon crystals were separated. 125 g of methanol, 375 g of toluene and 50 g of water were added to the resulting reaction mixture, and then 16% aqueous solution of sodium hydroxide, to neutralize the reaction mixture. Thereafter, 285 g of solvent were removed by distillation from the mixture and 150 g of water were added, and the separated crystals were collected by filtration. 259.5 g of 4,4'-bis(1-hydroxy-2-cyclohexyl-5-methylphenyl)methyl-2-benzyloxybenzene were obtained as white crystals having a purity of 99.7% in a yield of 98.3%.

Third Step (Production of 4,4'-bis(1-t-Butoxycarbonylmethoxy-2-cyclohexyl-5-methylphenyl)methyl-2-benzyloxybenzene)

86.4 g (0.15 mol) of 4,4'-bis(1-hydroxy-2-cyclohexyl-5-methylphenyl)methyl-2-benzyloxybenzene, 260 g of dimethylformamide and 62.3 g (0.45 mol) of potassium carbonate were placed in a flask. 67.7 g (0.45 mol) of t-butyl chloroacetate was added dropwise to the mixture at a temperature of 50° C. for one hour. After the addition, the mixture was stirred at a temperature of 70° C. for 24 hours, followed by another 4 hour stirring at a temperature of 100° C. The resulting reaction mixture was washed with 85 g of toluene and 300 g of water. The solvent was distilled out of the mixture at an inside temperature of 110° C. under a reduced pressure of 10 mmHg, and then 360 g of methanol and 20 g of toluene were added to the mixture. The separated crystals were collected by filtration, thereby providing 111.9 g of 4,4-bis (1-t-butoxycarbonylmethoxy-2-cyclohexyl-5-methylphenyl)methtl-2-benzyloxybenzene having a purity of 97.1% as white crystal in a yield of 90.3%.

Fourth Step (Production of 4,4'-bis(1-t-Butoxycarbonylmethoxy-2-cyclohexyl-5-methylphenyl)methyl-2-hydroxybenzene)

8.0 g (0.01 mol) of 4,4'-bis(1-t-butoxycarbonylmethoxy-2-cyclohexyl-5-methylphenyl)methyl-2-benzyloxybenzene, 80 g of tatrahydrofuran and 1.6 g of 5% palladium/carbon powder (having a water content of 50%) were placed in a flask. After the inside atmosphere was replaced with nitrogen gas, hydrogen gas was blown into the flask for eight hours at ordinary pressure at a temperature of 40° C. with stirring. After the completion of the reaction, the catalyst used was removed by filtration and then the solvent was removed by distillation under a reduced pressure of 30 mmHg from the reaction mixture. Toluene and methanol were added to the residue to crystallize the product. The crystals were collected by filtration to provide 4,4'-bis (1-t-butoxycarbonylmethoxy-2-cyclohexyl-5-methylphenyl)methyl-2-hydroxybenzene as white crystals having a purity of 97.4% (yield 90.1%). The total yield was 77.2%.

Melting point: 162.9° C. (DSC method); Infrared absorption spectrum (cm$^{-1}$): 3448.5: —OH; 1736.8: —C=O; 1604.7: Phenyl group; 1573.8: Phenyl group; Proton NMR Spectrum (400 MHz, DMSO-d$_6$ solvent):

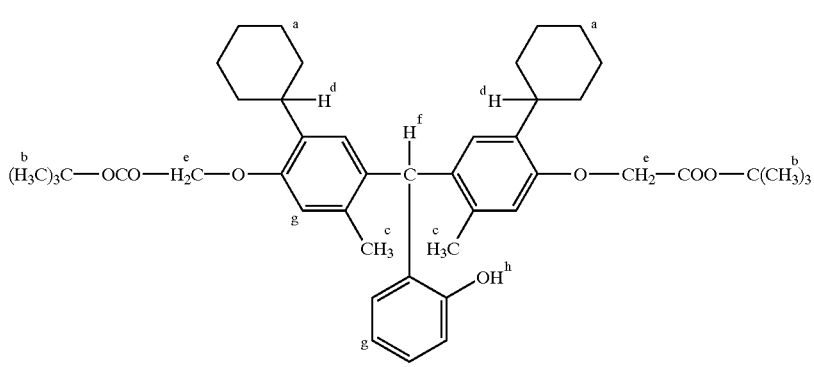

(1)

TABLE 1

| Chemical Shift (ppm) | Signal | Number of Protons | Assignment |
| --- | --- | --- | --- |
| 1.031–1.699 | m | 38 | a |
| 1.396 | s |  | b |
| 2.058 | s | 6 | c |
| 2.837 | s | 2 | d |
| 4.597 | s | 4 | e |
| 5.827 | s | 1 | f |
| 6.561–7.028 | m | 8 | g |
| 9.276 | s | 1 | h |

Example 2
(Production of 4,4'-bis(1-t-Butoxycarbonyloxy-2-cyclohexyl-5-methylphenyl)methyl-2-hydroxybenzene (2))

The first and second steps are the same as described in example 1.

Third Step
(Production of 4,4'-bis(1-t-Butoxycarbonyloxy-2-cyclohexyl-5-methylphenyl)methyl-2-benzyloxybenzene)

57.4 g (0.1 mol) of 4,4'-bis(1-hydroxy-2-cyclohexyl-5-methylphenyl)methyl-2-benzyloxybenzene, 8.6 g of dimethylformamide, 172 g of toluene and 1.4 g (0.01 mol) of potassium carbonate were placed in a flask. 58.9 g (0.27 mol) of di-t-butyl-carbonate were added dropwise to the mixture at a temperature of 70–94° C. over a period of 2.5 hours. After the addition, the mixture was stirred at a temperature of 100° C. for 15 hours and then the mixture was washed twice each with 100 g of water. The solvent was removed by filtration under a reduced pressure of 100 mmHg at an inside temperature of 65° C. to provide 62.4 g of 4,4'-bis(1-t-butoxycarbonyloxy-2-cyclohexyl-5-methylphenyl)methyl-2-benzyloxybenzene having a purity of 98.6% as pale yellow solid bottom in a yield of 91.2%.

Fourth Step
(Production of 4,4'-bis(1-t-Butoxycarbonyloxy-2-cyclohexyl-5-methylphenyl)methyl-2-hydroxybenzene)

9.0 g (0.0116 mol) of 4,4'-bis(1-t-butoxycarbonyloxy-2-cyclohexyl-5-methylphenyl)methyl-2-benzyloxybenzene, 80 g of tetrahydrofuran and 1.8 g of 5% palladium/carbon powder (having a water content of 50%) were placed in a flask. After the inside atmosphere was replaced with nitrogen gas, hydrogen gas was blown into the flask for 24 hours at ordinary pressure at a temperature of 40–60° C. with stirring.

After the completion of the reaction, the catalyst used was removed by filtration and then the solvent was removed by distillation under a reduced pressure of 14 mmHg from the reaction mixture, thereby providing 8.1 g of 4,4'-bis (1-t-butoxycarbonyloxy-2-cyclohexyl-5-methylphenyl)methyl-2-hydroxybenzene having a purity of 97.9% as white glassy solid in a yield of 100%.

Melting point: (not measurable because the product was glassy solid); Infrared absorption spectrum (cm$^{-1}$): 3468.7: —OH; 1757.0: —C=O; 1498.6: Phenyl group; 1455.2: Phenyl group; Proton NMR Spectrum (400 MHz, DMSO-d$_6$ solvent):

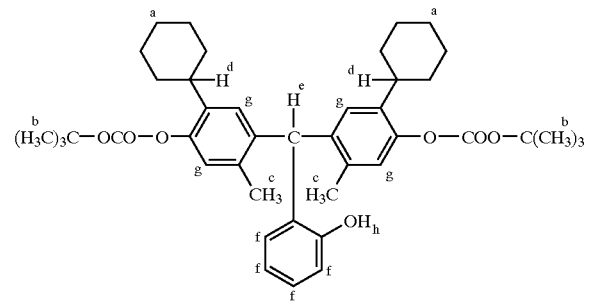

(2)

TABLE 2

| Chemical Shift (ppm) | Signal | Number of Protons | Assignment |
| --- | --- | --- | --- |
| 1.026–1.760 | m | 20 | a |
| 1.476 | s | 18 | b |
| 1.472 | s |  |  |
| 2.093 | s | 6 | c |
| 2.426–2.509 | m | 2 | d |
| 5.926 | s | 1 | e |
| 6.553 | d | 4 | f |
| 6.763 | t |  |  |
| 6.841 | d |  |  |
| 7.073 | t |  |  |
| 6.677 | s | 4 | g |
| 6.892 | s |  |  |
| 9.482 | s | 1 | h |

Example 3
(Production of 4,4'-bis(1-Tetrahydropyranyloxy-2-cyclohexyl-5-methylphenyl)methyl-2-hydroxybenzene (3)))

The first and second steps are the same as those described in Example 1.

Third Step
(Production of 4,4'-bis(1-Tetrahydropyranyloxy-2-cyclohexyl-5-methylphenyl)methyl-2-benzyloxybenzene)

28.9 g (0.05 mol) of 4,4'-bis(1-hydroxy-2-cyclohexyl-5-methylphenyl)methyl-2-benzyloxybenzene and 0.094 g of p-toluenesulfonic acid monohydrate were placed in flask together with 90 g of ethyl acetate to prepare a solution. 25.2 g (0.03 mol) of 3,4-dihydro-2H-pyran were added dropwise to the solution for one hour at a temperature of 20–27° C., followed by stirring for seven hours at a temperature of 20° C., whereupon crystals were formed out of the solution. The crystals were collected by filtration and dried to provide 22.0 g of 4,4'-bis(1-tetrahydropyranyloxy-2-cyclohexyl-5-methylphenyl)methyl-2-benzyloxybenzene as white crystals in a yield of 59.3%.

Fourth Step
(Production of 4,4'-bis(1-Tetrahydropyranyloxy-2-cyclohexyl-5-methylphenyl)methyl-2-hydroxybenzene)

11.6 g of (0.0156 mol) of 4,4'-bis(1-tetrahydropyranyloxy-2-cyclohexyl-5-methylphenyl)methyl-2-benzyloxybenzene, 150 g of tetrahydrofuran and 3.5 g of 5% palladium/carbon powder (having a water content of 50%) were placed in a flask. After the inside atmosphere was replaced with nitrogen gas, hydrogen gas was blown into the flask for eight hours at ordinary pressure at a temperature of 20–30° C. with stirring.

Stirring was ceased and the reaction mixture was left standing overnight to complete the reaction. The catalyst used was removed by filtration and then the solvent was removed by distillation under a reduced pressure of 20 mmHg from the reaction mixture, thereby providing 11.0 g of white glassy solid containing 4,4'-bis(1-tetrahydropyranyloxy-2-cyclohexyl-5-methylphenyl)methyl-2-hydroxybenzene in an amount of 77%. The product was purified using a silica gel column wherein an eluent composed of 70% heptane and 30% ethyl acetate was used to provide 4,4'-bis(1-tetrahydropyranyloxy-2-cyclohexyl-5-methylphenyl)methyl-2-hydroxybenzene having a purity of 97.5% as white glassy solid in a yield of 33%.

Melting point: (not measurable because the product was glassy solid) Infrared absorption spectrum (cm$^{-1}$): 3369.4: —OH; 2925.8: alkyl group; 1608.5: Phenyl group; 1573.8: Phenyl group; Proton NMR Spectrum (400 MHz, CDCl$_3$ solvent):

TABLE 3

| Chemical Shift (ppm) | Signal | Number of Protons | Assignment |
| --- | --- | --- | --- |
| 1.117–1.868 | m | 32 | a, b |
| 2.121 | s | 6 | c |
| 2.126 | s | | |
| 2.797–2.816 | m | 2 | d |
| 3.613–3.638 | m | 2 | e |
| 3.895–3.922 | m | 2 | |
| 4.910 | m | 1 | f |
| 5.380–5.409 | m | 2 | g |
| 5.631 | m | 1 | h |
| 6.637 | m | 3 | i |
| 6.647 | | | |
| 6.856 | | | |
| 6.754–6.784 | m | 2 | |
| 6.884–6.891 | m | 2 | |
| 7.074–7.098 | m | 1 | |

Example 4
(Production of 2,2'-bis(1-t-Butoxycarbonylmethoxy-3,5-dimethylphenyl)methyl-3-methoxy-4-hydroxybenzene (4))

First Step
(Production of 3-Methoxy-4-benzyloxybenzaldehyde)

76 g (0.5 mol) of 3-methoxy-4-hydroxybenzaldehyde were placed in a four-necked flask together with 228 g of dimethylformamide and 82.8 g (0.6 mol) of potassium carbonate. 66.4 g (0.525 mol) of benzyl chloride was added dropwise at a temperature of 60° C. for one hour. After the addition, the mixture was stirred at a temperature of 60° C. for five hours. The resulting reaction mixture was washed with 190 g of toluene and 330 g of water. 270 g of the solvent were removed by distillation under reduced pressure of 70 mmHg and then 265 g of n-heptane and 80 g of toluene were added to the distillation residue and the separated crystals were collected by filtration to provide 102.6 g of 3-methoxy-4-benzyloxybenzaldehyde as white crystals in a yield of 84.8%.

Second Step
(Production of 2,2'-bis(1-Hydroxy-3,5-dimethylphenyl)methyl-3-methoxy-4-benzyloxybenzene)

12.1 g (0.05 mol) of 3-methoxy-4-benzyloxybenzaldehyde were placed in a flask together with 18.3 g (0.15 mol) of 3,5-dimethylphenol, 3 g of methanol and 1.2 g of 35% hydrochloric acid and the mixture was reacted at a temperature of 50° C. for two hours. After the reaction, 36 g of toluene and 8% sodium hydroxide aqueous solution were added to the reaction mixture to neutralize the hydrochloric acid in the reaction mixture and then the resulting oily layer was separated. 0.5 g of phosphoric acid were added to the oily layer to effect neutralization After washing, the oily layer was subjected to distillation under reduced pressure of 4 mmHg to remove the solvent from the oily layer. 18 g of toluene were added to the distillation residue and 9.2 g of crude crystals were collected by filtration. 9.2 g of the crude crystals were recrystallized from 28 g of toluene to provide 6.1 g of 2,2'-bis(1-hydroxy-3,5-dimethylphenyl)methyl-3-methoxy-4-benzyloxybenzene having a purity of 98.1% in a yield of 25.6%.

Third Step
(Production of 2,2'-bis(1-t-Butoxycarbonylmethoxy-3,5-dimethylphenyl)methyl-3-methoxy-4-benzyloxybenzene)

5.9 g (0.0143 mol) of 2,2'-bis(1-hydro-3,5-dimethylphenyl)methyl-3-methoxy-4-benzyloxybenzene, 18 g of dimethylformamide and 4.6 g (0.033 mol) of potassium carbonate were placed in a flask together with 5.2 g (0.035 mol) of t-butyl chloroacetate and the mixture was reacted at a temperature of 70° C. for 22 hours. The resulting reaction mixture was washed with 18 g of toluene and 18 g of water. The solvent was removed from the mixture by

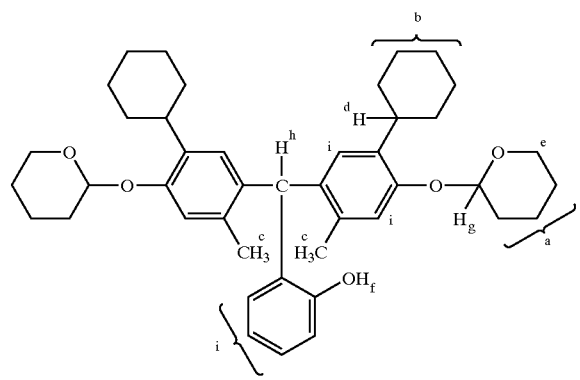

(3)

distillation under reduced pressure of 6 mmHg and an inside temperature of 100° C. to provide 10.7 g of 2,2'-bis(1-t-butoxycarbonylmethoxy-3,5-dimethylphenyl)methyl-3-methoxy-4-benzyloxybenzene as yellow syrup in a yield of 100%.

Fourth Step
(Production of 2,2'-bis(1-t-Butoxycarbonylmethoxy-3,5-dimethylphenyl)methyl-3-methoxy-4-hydroxybenzene)

10.7 g (0.015 mol) of 2,2'-bis(1-t-butoxycarbonylmethoxy-3,5-dimethylphenyl)methyl-3-methoxy-4-benzyloxybenzene, 100 g of tetrahydrofuran and 2.1 g of 5% palladium/carbon powder (having a water content of 50%) were placed in a flask. After the inside atmosphere was replaced with nitrogen gas, hydrogen gas was blown into the flask for six hours at ordinary pressure at a temperature of 40° C. with stirring. After the reaction, the catalyst used was removed from the resulting reaction mixture by filtration and then the solvent was removed by distillation under reduced pressure of 10 mmHg. 15 g of n-heptane were added to the distillation residue to effect crystallization to provide 5.9 g of white crystals.

The crystals were recrystallized from a solvent mixture of ethyl acetate and n-heptane to provide 3.2 g of 2,2'-bis(1-t-butoxycarbonylmethoxy-3,5-dimethylphenyl)methyl-3-methoxy-4-hydroxybenzene having a purity of 96.8% in a yield of 40.7%. The overall yield was 8.8%.

Melting point: 124.1° C. (DSC method); Infrared absorption spectrum (cm$^{-1}$): 3488.0: —OH; 2979.8: alkyl group; 1750.3: —C=O; 1610.5: Phenyl group; 1521.1: Phenyl group; Proton NMR spectrum (400 MHz, DMSO-d$_6$ solvent):

(4)

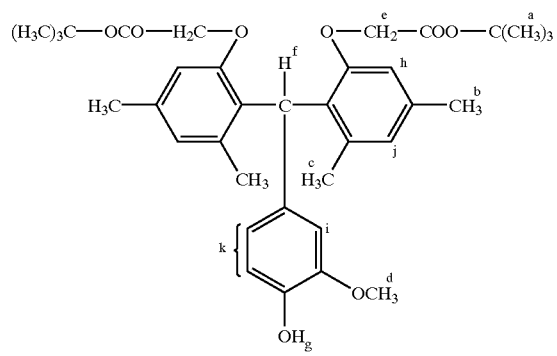

TABLE 4

| Chemical Shift (ppm) | Signal | Number of Protons | Assignment |
|---|---|---|---|
| 1.429 | s | 18 | a |
| 1.432 | s | | |
| 2.017 | s | 6 | b, c |
| 2.228 | s | 6 | |
| 3.751 | d | 3 | d |
| 3.941 | s | 4 | e |
| 5.475 | d | 1 | f |
| 6.149 | s | 1 | g |
| 6.406 | s | 2 | h |
| 6.554 | m | 1 | i |
| 6.574 | s | 2 | j |
| 5.707–6.730 | m | 2 | k |

Production of the Second One of the Partially Protected Trisphenols of the Invention Example 5
(Production of 2-t-Butoxycarbonylmethoxybenzaldehyde)

366 g of dimethylformamide and 165.9 g (1.2 mol) of potassium carbonate were placed in a flask, followed by dropwise addition of 122 g (1 mol) of salicylaldehyde. 181.2 g (1.2 mol) of t-butyl chloroacetate were added dropwise to the mixture at a temperature of 50° C. for three hours. After the addition, the mixture was stirred for three hours at a temperature of 50° C. The resulting reaction mixture was washed with 122 g of toluene and 662 g of water. 130 g of the solvent was removed from the mixture by distillation and then 122 g of n-heptane were added to the distillation residue to effect crystallization. The resulting crystals were collected by filtration to provide 122.3 g of 2-t-butoxycarbonylmethoxybenzaldehyde having a purity of 98.5% as brown or pale yellow crystals. The filtrate was concentrated and provided 52.6 g of 2-t-butoxycarbonylmethoxybenzaldehyde having a purity of 98.0%. FIG. 1 is an infrared absorption spectrum of the compound. The overall yield was 74%.

Melting point: 68.6° C. (DSC method) Proton NMR spectrum (60 MHz, CDCl$_3$ solvent, δ (ppm)):

TABLE 5

| Chemical Shift (δ) | Number of Protons | Assignment |
|---|---|---|
| 1.48 (s) | 9 | t-butyl |
| 4.62 (s) | 2 | methylene |
| 6.74–7.90 (m) | 4 | phenyl |
| 10.56 (s) | 1 | aldehyde group |

Example 6
(Production of 4-t-Butoxycarbonylmethoxybenzaldehyde)

Figure 2:
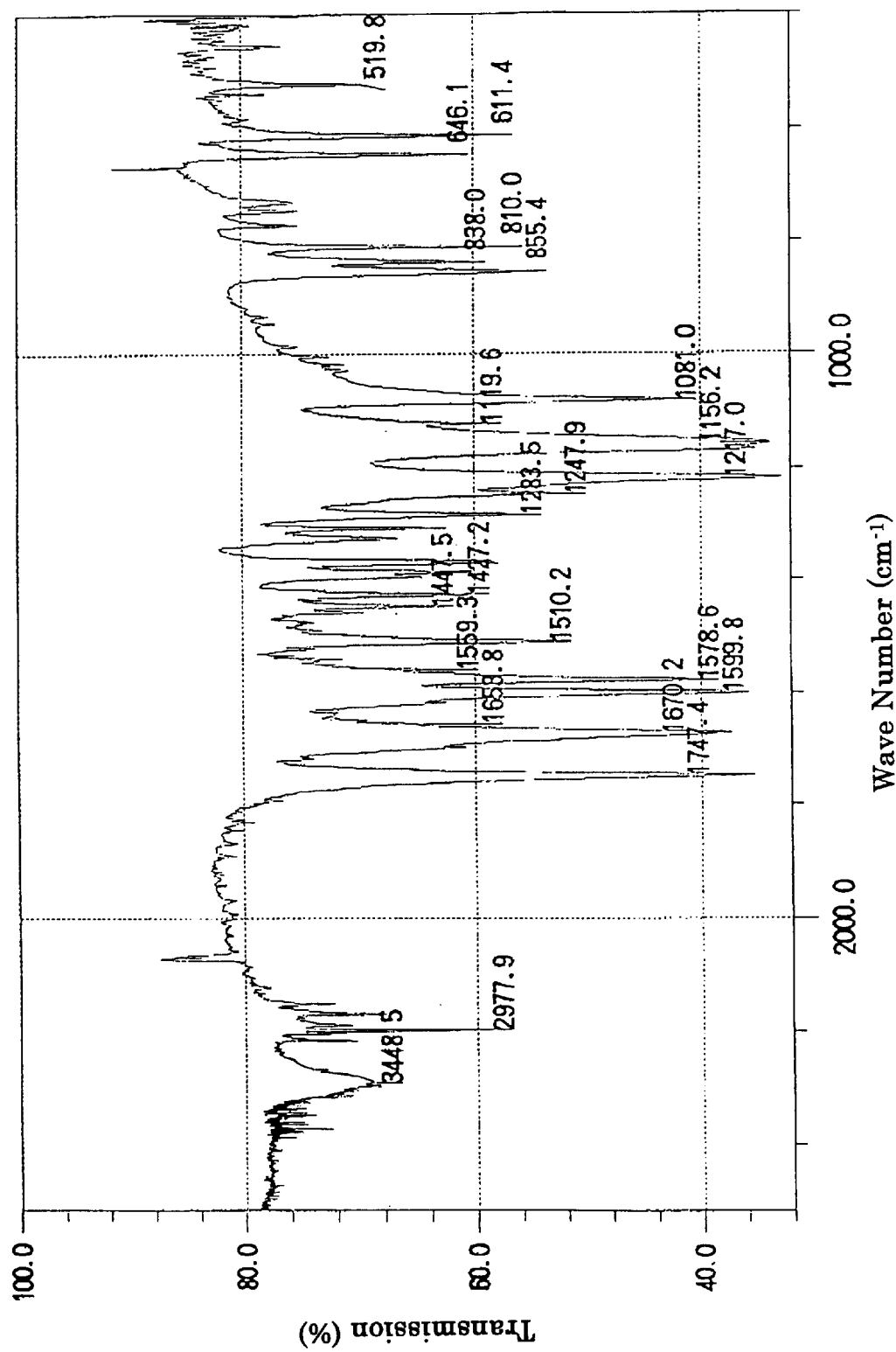
FIG. 2 is an infrared absorption spectrum of 4-t-butoxycarbonylmethoxybenzaldehyde of the invention.

366 g of dimethylformamide and 165.9 g (1.2 mol) of potassium carbonate were placed in a flask, followed by dropwise addition of 122 g (1 mol) of 4-hydroxybenzaldehyde. 181.2 g (1.2 mol) of t-butyl chloroacetate were added dropwise to the mixture at a temperature of 50° C. for two hours. After the addition, the mixture was stirred for two hours at a temperature of 50° C. and then another seven hours at a temperature of 70° C. The resulting reaction mixture was washed with 122 g of toluene and 662 g of water. 100 g of the solvent was removed from the mixture by distillation under reduced pressure and then 236 g of n-heptane were added to the distillation residue to effect crystallization. The resulting crystals were collected by filtration to provide 128.4 g of 4-t-butoxycarbonylmethoxybenzaldehyde having a purity of 99.9% as white crystals. FIG. 2 is an infrared absorption spectrum of the compound. The yield was 54%.

Melting point: 58.4° C. (DSC method); Proton NMR spectrum (60 MHz, CDCl$_3$ solvent, δ (ppm)):

TABLE 6

| Chemical Shift (δ) | Number of Protons | Assignment |
|---|---|---|
| 1.43 (s) | 9 | t-butyl |
| 4.60 (s) | 2 | methylene |
| 6.92, 7.60 (d) | 4 | phenyl |
| 7.76, 7.91 (d) | | |
| 9.88 (s) | 1 | aldehyde group |

Example 7

Production of 4,4'-bis(1-Hydroxy-2-cyclohexyl-5-methylphenyl)methyl-2-t-butoxycarbonylmethoxybenzene 38 g (0.2 mol) of 3-methyl-6-cyclohexylphenol, 20 g of methanol and 4.8 g of 35% hydrochloric acid were placed in a flask and the mixture was put at a temperature of 0° C. 23.6 g (0.1 mol) of 2-t-butoxycarbonylmethoxybenzaldehyde obtained in Example 5 were added dropwise intermittently to the mixture at a temperature of 0° C. over a period of one hour. The mixture was then stirred at a temperature of 0° C. for seven hours and then at room temperature for another 13 hours. 48 g of toluene were added to the reaction mixture and then 50 g of 8% sodium hydroxide aqueous solution to wash the mixture. After washing with water, the mixture was washed with 50 g of 1% oxalic acid aqueous solution. After further washed with water, the reaction mixture was subjected to distillation under reduced pressure at an inside temperature of 90° C. or less to remove the solvent therefrom. 100 g of n-heptane were added to the distillation residue to effect crystallization. The resulting crystals were collected by filtration to provide 43.0 g of white crystals containing 4,4'-bis(1-hydroxy-2-cyclohexyl-5-methylphenyl)methyl-2-t-butoxycarbonylmethoxybenzene in an amount of 92.5% in a yield of 72%. The crystals were recrystallized from cyclohexane.

Melting point: 178.7° C. (Mettler method); Infrared absorption spectrum (cm$^{-1}$): 3446: vOH; 1732: vCOO; Proton NMR spectrum (60 MHz, DMSO-d$_6$ solvent, δ (ppm)):

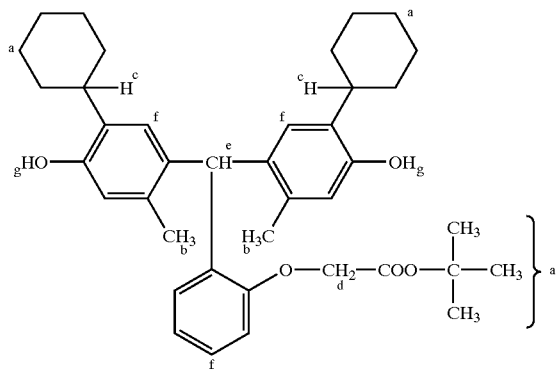

TABLE 7

| Chemical Shift (δ) | Number of Protons | Assignment |
|---|---|---|
| 0.52–2.03 | 29 | a |
| 1.43 | | |
| 2.03 | 6 | b |
| 2.76 | 2 | c |
| 4.47 | 2 | d |
| 5.95 | 1 | e |
| 6.57–7.16 | 8 | f |
| 8.76 | 2 | g |

What is claimed is:

1. A partially protected trisphenol having the general formula (I)

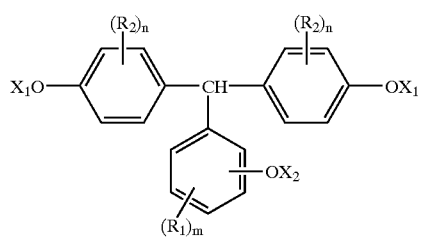

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_1$ is a hydrogen atom, an alkoxycarbonylmethyl group wherein the alkyl group has 1–4 carbons, an alkoxycarbonyl group wherein the alkyl group has 1–4 carbons or a tetrahydropyranyl group, $X_2$ is a hydrogen atom, an alkoxycarbonylmethyl group wherein the alkyl group has 1–4 carbons, an alkoxycarbonyl group wherein the alkyl group has 1–4 carbons or a tetrahydropyranyl group, provided that when $X_1$ is a hydrogen atom, $X_2$ is not a hydrogen atom, and when $X_2$ is a hydrogen atom, $X_1$ is not a hydrogen atom; and m is an integer of 0, 1 or 2, and n is an integer of 0, 1, 2 or 3.

2. A partially protected trisphenol as claimed in claim 1 which has the general formula (Ia)

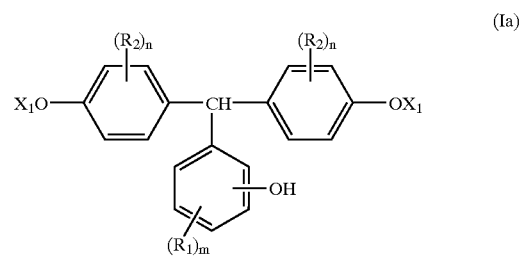

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_1$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and n is an integer of 0, 1, 2 or 3.

3. A partially protected trisphenol as claimed in claim 1 which has the general formula (Ib)

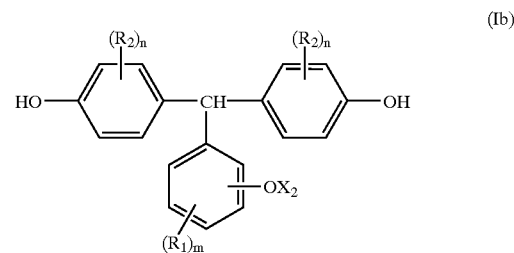

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $X_2$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and n is an integer of 0, 1, 2 or 3.

4. A partially protected trisphenol as claimed in claim 3 which has the general formula (Ic)

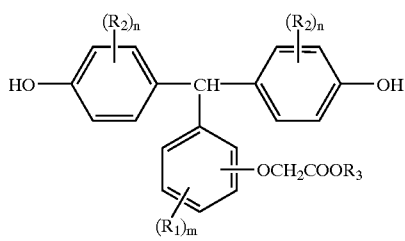

(Ic)

wherein $R_1$ is an alkyl group of 1–4 carbons or an alkoxyl group of 1–4 carbons, $R_2$ is an alkyl group of 1–6 carbons or a cycloalkyl group of 5 or 6 carbons, $R_3$ is an alkyl group of 1–4 carbons; and m is an integer of 0, 1 or 2, and n is an integer of 0, 1, 2 or 3.

5. A process for production of a partially protected trisphenol as claimed in claim 2 which comprises:

the first step wherein a hydroxybenzaldehyde having the general formula (II)

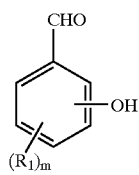

(II)

wherein $R_1$ is an alkyl group of 1–4 carbons or an alkoxyl group of 1–4 carbons; and m is an integer of 0, 1 or 2, and when m is 2, $R_1$'s may be the same or different from each other, is reacted with a benzyl halide in the presence of an alkali, to prepare a benzyloxybenzaldehyde having the general formula (III)

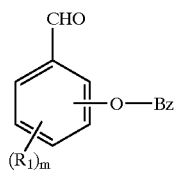

(III)

wherein $R_1$ and m are the same as hereinbefore defined, and Bz is a benzyl group;

the second step wherein the benzyloxybenzaldehyde is reacted with a phenol having the general formula (IV)

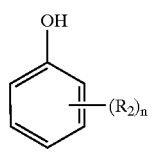

(IV)

wherein $R_2$ is an alkyl group of 1–6 carbons or a cycloalkyl group of 5 or 6 carbons; and n is an integer of 0, 1, 2 or 3, and when n is 2 or more, $R_2$'s may be the same or different from each other, in the presence of an acid catalyst, to prepare a monobenzylated trisphenol having the general formula (V)

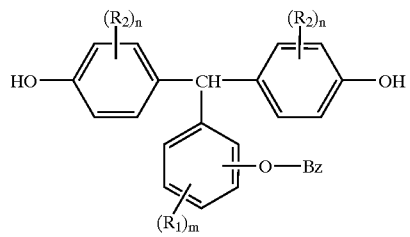

(V)

wherein $R_1$, $R_2$, Bz, m and n are the same as hereinbefore defined;

the third step wherein the monobenzylated trisphenol is reacted with a protecting agent selected from the group consisting of a haloacetic acid alkyl ester wherein the alkyl group has 1–4 carbons, a dialkyl carbonate wherein each of the alkyl groups has 1–4 carbons and 2,3-dihydro-4-H-pyran, thereby protecting the two hydroxyl groups in the molecule of the monobenzylated trisphenol, to prepare a trisphenol in which the hydroxyl groups are thus protected and which has the general formula (VI)

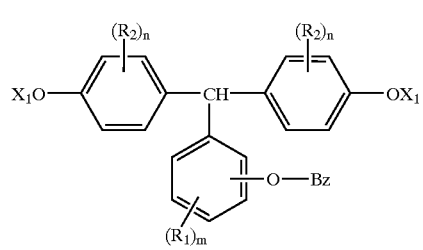

(VI)

wherein $R_1$, $R_2$, Bz, m and n are the same as hereinbefore defined; and $X_1$ is a protecting group selected from the group consisting of an alkoxycarbonylmethyl group wherein the alkyl group has 1–4 carbons, an alkoxycarbonyl group wherein the alkyl group has 1–4 carbons and a tetrahydropyranyl group; and the fourth step wherein the trisphenol in which the two hydroxyl groups are thus protected is subjected to hydrogenolysis in the presence of a hydrogenolysis catalyst.

6. A process for production of a partially protected trisphenol as claimed in claim 3 which comprises: reacting a benzaldehyde in which the hydroxyl group is protected and which has the general formula (VII)

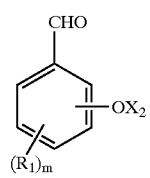

(VII)

wherein $R_1$ is an alkyl group of 1–4 carbons or an alkoxyl group of 1–4 carbons, $X_2$ is an alkoxycarbonylmethyl group wherein the alkyl group has 1–4 carbons, an alkoxycarbonyl group wherein the alkyl group has 1–4 carbons or a tetrahydropyranyl group; and m is an integer of 0, 1 or 2, and when m is 2, $R_1$'s may be the same or different from each other, with a phenol having the general formula (VIII)

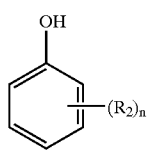

(VIII)

wherein $R_2$ is an alkyl group of 1–6 carbons or a cycloalkyl group of 5 or 6 carbons, $R_3$ is an alkyl group of 1–4 carbons; and n is an integer of 0, 1, 2 or 3, and when n is 2 or 3, $R_2$'s may be the same or different from each other, in the presence of an acid catalyst.

7. A process for production of a partially protected trisphenol as claimed in claim 4 which comprises: reacting an alkoxycarbonylmethoxybenaldehyde having the general formula (IX)

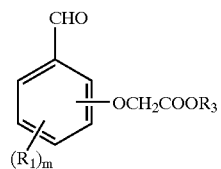

(IX)

wherein $R_1$ is an alkyl group of 1–4 carbons or an alkoxyl group of 1–4 carbons, $R_3$ is an alkyl group of 1–4 carbons; and m is an integer of 0, 1 or 2, and when m is 2, $R_1$'s may be the same or different from each other, with a phenol having the general formula (VIII)

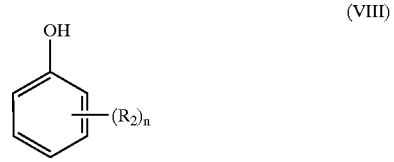

(VIII)

wherein $R_2$ is an alkyl group of 1–6 carbons or a cycloalkyl group of 5 or 6 carbons; and n is an integer of 0, 1, 2 or 3, and when n is 2 or 3, $R_2$'s may be the same or different from each other, in the presence of an acid catalyst.

* * * * *